(12) United States Patent
Forster

(10) Patent No.: US 8,941,371 B2
(45) Date of Patent: *Jan. 27, 2015

(54) RFID SENSOR DEVICES HAVING DRIVE ELEMENTS

(75) Inventor: Ian J. Forster, Essex (GB)

(73) Assignee: Avery Dennison Corporation, Glendale, CA (US)

(*) Notice: Subject to any disclaimer, the term of this patent is extended or adjusted under 35 U.S.C. 154(b) by 555 days.

This patent is subject to a terminal disclaimer.

(21) Appl. No.: 13/210,634

(22) Filed: Aug. 16, 2011

(65) Prior Publication Data

US 2013/0043860 A1 Feb. 21, 2013

(51) Int. Cl.
| | |
|---|---|
| G01N 27/00 | (2006.01) |
| G01R 27/04 | (2006.01) |
| H04Q 5/22 | (2006.01) |
| H04Q 9/00 | (2006.01) |
| G06K 19/07 | (2006.01) |
| G01N 27/22 | (2006.01) |
| G01N 27/04 | (2006.01) |

(52) U.S. Cl.
CPC .............. *H04Q 9/00* (2013.01); *G06K 19/0723* (2013.01); *G01N 27/221* (2013.01); *G01N 27/041* (2013.01); *H04Q 2209/47* (2013.01)
USPC .......................... 324/71.1; 324/629; 340/10.1

(58) Field of Classification Search
CPC . G06K 19/0723; H04Q 2209/47; H04Q 9/00; G01N 27/221
USPC ................................. 324/629, 71.1; 340/10.1
See application file for complete search history.

(56) References Cited

U.S. PATENT DOCUMENTS

| | | | |
|---|---|---|---|
| 6,349,671 B1* | 2/2002 | Lewis et al. ................ | 119/51.02 |
| 2008/0135614 A1 | 6/2008 | Werner et al. | |
| 2009/0152364 A1 | 6/2009 | Spivey | |
| 2011/0309937 A1* | 12/2011 | Bunza et al. ............... | 340/573.5 |
| 2013/0144133 A1* | 6/2013 | Forster .......................... | 600/309 |

OTHER PUBLICATIONS

"ElectroActive Polymers—EAPs", Dr. Yoseph Bar-Cohen, Sep. 17, 2001.

* cited by examiner

*Primary Examiner* — Amy He
(74) *Attorney, Agent, or Firm* — Avery Dennison Retail Information Services LLC

(57) ABSTRACT

An RFID-based sensor is provided with an RFID chip and an antenna electrically connected to the RFID chip. The sensor further includes a sensing material electrically connected to the antenna and a drive element. At least a portion of the sensor is movable between a closed condition in which the sensing material is isolated from the outside environment and an open condition in which the sensing material is exposed to the outside environment. The drive element moves the sensor between the open and closed configurations depending on whether or not it is receiving a signal.

7 Claims, 5 Drawing Sheets

RFID SENSOR DEVICES HAVING DRIVE ELEMENTS

FIELD OF THE DISCLOSURE

The present subject matter relates to radio frequency identification ("RFID") sensor devices. More particularly, the present subject matter relates to RFID sensor devices having components which are movable relative to each other upon an applied vibration.

DESCRIPTION OF RELATED ART

Electrically powered devices for sensing a material or condition are well known. Recently, sensors incorporating RFID technology have been proposed as a means for providing a sensing function at a relatively low power requirement. Exemplary sensors incorporating RFID technology are described in U.S. Patent Application Publication No. 2008/0135614 to Werner et al., which is incorporated herein by reference. Such devices typically include material which is sensitive to a substance (e.g., an analyte) and an antenna electrically connected to each other. When the antenna is energized, it sends a signal to a receiver device or controller which analyzes the signal. One or more of the electrical properties of the sensing material (typically its resistance) change when in the presence of the substance, which modifies the signal being transmitted by the antenna. The controller is programmed to analyze the modified signal and produce an output indicative of the presence of the substance in the vicinity of the sensing material and/or one or more properties of the substance.

It may be desirable for the sensing material of the sensor to be temporarily and/or selectively isolated from the outside environment. Accordingly, sensors incorporating a mechanism for moving the sensor between a closed or inactive condition and an open or active condition are advantageous.

SUMMARY OF THE INVENTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one aspect, an RFID-based sensor is provided with an RFID chip and an antenna electrically connected to the RFID chip. The sensor further includes a sensing material electrically connected to the antenna, first and second layers, and a drive element. The drive element is configured to move at least a portion of the first and/or second layers with respect to each other upon receiving a signal.

In another aspect, an RFID-based sensor is provided with an RFID chip and an antenna electrically connected to the RFID chip. The sensor further includes a drive element, a sensing material electrically connected to the antenna, and a gate member. The drive element is configured to move at least a portion of the gate member with respect to the sensing material upon receiving a signal.

In yet another aspect, a method is provided for exposing a sensor to an environment. The method includes providing a sensor having a sensing material and a drive element and isolating the sensing material from an environment. A signal is sent to the drive element, thereby causing the drive element to move at least a portion of the sensor with respect to the sensing material and exposing the sensing material to the environment.

DESCRIPTION OF THE ILLUSTRATED EMBODIMENTS

The embodiments disclosed herein are exemplary only, and the subject matter described herein may be embodied in various forms. Therefore, specific details disclosed herein are not to be interpreted as limiting the subject matter as defined in the accompanying claims.

Figure 1:
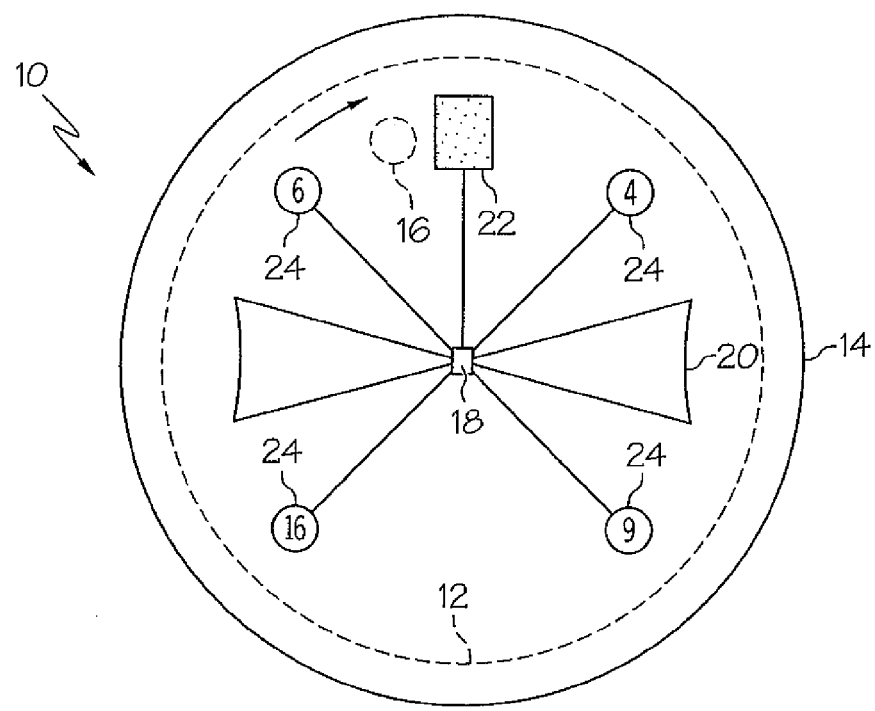
FIG. 1 is a top plan view of an RFID-based sensor featuring selective rotational movement, with the sensor being shown in a closed condition.
Figure 2:
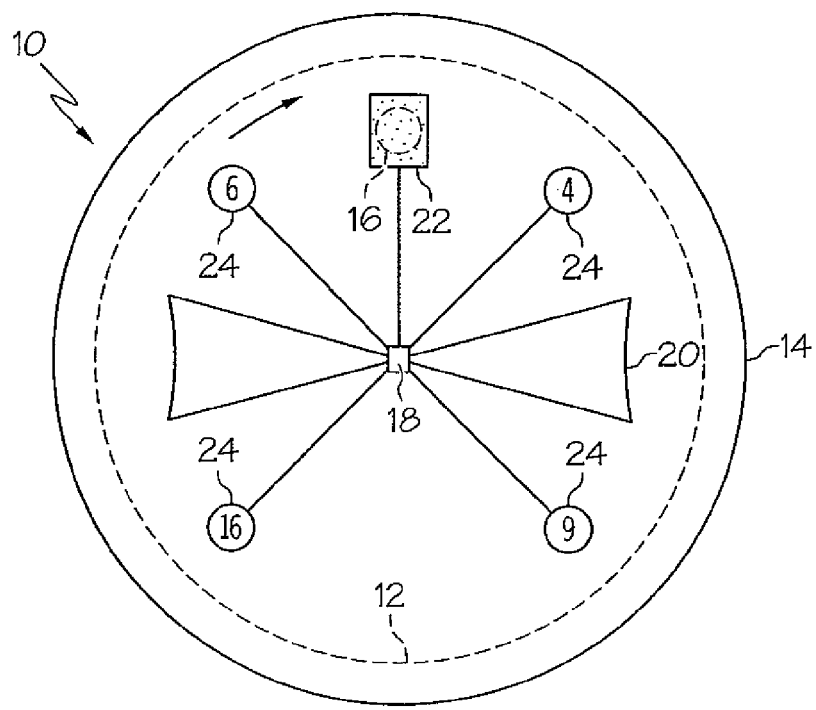
FIG. 2 is a top plan view of the RFID-based sensor of FIG. 1 in an open condition.

FIGS. 1 and 2 show an RFID-based device or sensor 10 according to the present disclosure. The sensor 10 comprises an upper or first layer 12 (shown in broken lines in FIGS. 1 and 2 for illustrative purposes) and a lower or second layer 14. The upper layer 12 includes at least one aperture 16 passing through the thickness of the upper layer 12. While the upper layer 12 is illustrated with a single aperture 16, it may include a plurality of apertures without departing from the scope of the present disclosure. As will be described in greater detail below, the first and/or second layers 12 and 14 are rotationally movable with respect to each other to reorient the aperture 16 between a closed or non-operational condition (FIG. 1) and an open or operational condition (FIG. 2).

An RF communication chip 18, which may include an integrated circuit for controlling RF communication and other functions of the sensor 10, is associated with one of the layers. In the illustrated embodiment, the chip 18 is associated with the lower layer 14.

The RF communication chip 18 is electrically connected or coupled to an antenna 20 which, in the illustrated embodiment, is associated with the same layer as the chip 18, but may be spaced away from the chip 18 in other embodiments. The antenna 20 is adapted to receive energy from an RF field and produce a signal which is transmitted to one or more external devices, such as a controller or reader or detector, which receives and analyzes the signal. The RF field may be generated by the device to which the antenna 20 transmits the signal or it may be generated by a different external device. The antenna 20 may be any of a variety of antenna types, such as a dipole antenna, loop antenna, slot antenna, or a hybrid combining characteristics of these antenna types.

The antenna 20 is electrically connected or coupled to at least one sensing material 22. In the illustrated embodiment, the sensing material 22 is associated with the same layer as the chip 18, but may be spaced away from the chip 18 without departing from the scope of the present disclosure. The sensing material 22 has an electrical property which varies in the presence of a particular substance or condition. For example, the sensing material 22 may be adapted to have a dielectric constant or conductivity which changes when the sensing material 22 is in contact with or in the vicinity of the substance or condition. The signal produced by the antenna 20 will change when the electrical property of the sensing material 22 changes. Accordingly, if the signal transmitted by the antenna 20 is the same before and after the sensing material 22 is placed in fluid communication with an environment, it is indicative that there is none (or an insufficient amount) of the substance or condition present in the environment. On the other hand, if the RFID reader detects a difference between the signals, it is indicative that the substance or condition is present in the environment.

The sensor 10 further includes at least one drive element 24 electrically connected or coupled to the chip 18. In the illustrated embodiment, the drive element 24 is associated with the same layer as the chip 18, but may be spaced away from the chip 18 in other embodiments. The drive element 24 may be variously configured. In one embodiment, the drive element comprises an electroactive polymer, for example a dielectric EAP, ferroelectric polymer, liquid crystal or ionic polymer material. In another embodiment the drive element is piezoelectric, for example a lead zirconate titanate or a polymer such as polyvinylidene fluoride. The drive element 24 may be mounted on a surface of the sensor 10, printed thereon, formed by using a suitable material for the substrate layer (e.g., polyvinylidene fluoride) to make the layer piezoelectric in selected areas, or associated therewith by any other suitable means.

The drive element 24 is adapted such that a mechanical stress is induced therein upon receiving an electrical signal from the chip 18. The drive element 24 is associated with the layers 12 and 14 in such a way that the stress manifests itself in the form of a mechanical vibration which causes rotational movement of the upper layer 12 with respect to the lower layer 14. The response may be modified by processes such as cutting or embossing. The upper layer 12 is either free to move or is attached to the lower layer 14 by a material having a defined elasticity so that, when a rotational force is applied, a known angle of rotation is achieved.

In this illustrated embodiment, when the piezoelectric drive element 24 is not receiving a signal from the chip 18, the sensor 10 is in the closed condition of FIG. 1, with the aperture 16 of the upper layer 12 substantially misaligned with the sensing material 22. When the aperture 16 and the sensing material 22 are substantially misaligned, the sensing material 22 is isolated from the outside environment and is, therefore, in an inoperative condition. When the drive element 24 receives a signal from the chip 18, it reacts so as to cause the upper layer 12 to rotate and place the aperture 16 into substantial alignment with the sensing material 22 (FIG. 2), which places the sensing material 22 in fluid communication with the outside environment (via the aperture 16) and allows the sensor 10 to analyze the outside environment. The misalignment of the sensing material 22 and the aperture 16 may be relatively small, thereby minimizing the rotational movement that must be induced in the sensor 10 to align them.

When the signal is removed or if a different signal is received by the drive element 24, the sensor 10 may return to the closed condition (FIG. 1) or to a different or a third condition. Removing or changing the signal so as to return the sensor 10 to the closed condition may cause some material from the outside environment to become trapped in the sensor 10 (i.e., above the sensing material 22 and below the upper layer 12), which may be advantageous in some applications.

While the foregoing description concerns an embodiment with the sensor 10 being in the closed condition by default (i.e., when not receiving a signal), it is within the scope of the present disclosure for the sensor 10 to be in the open condition by default and move to the closed condition when receiving a signal.

The upper layer 12 may be provided with a plurality of apertures 16 and the lower layer 14 provided with a plurality of sensing materials 22, with one or more apertures 16 positioned so as to be substantially aligned with one of the sensing materials 22 at the same or different rotational degrees. The sensor 10 may be configured such that the sensing materials 22 are sequentially or simultaneously exposed to the outside environment by relative rotation of the layers. This allows a sensing material 22 to be exposed for a defined time, which is advantageous for quantitative analysis purposes. It is also within the scope of the present disclosure for the aperture 16 to have a range of degrees to which it is aligned with the sensing material 22, in which case the flow rate of fluid from the outside environment to the sensing material 22 may be controlled by controlling the degree of alignment.

Figure 3:
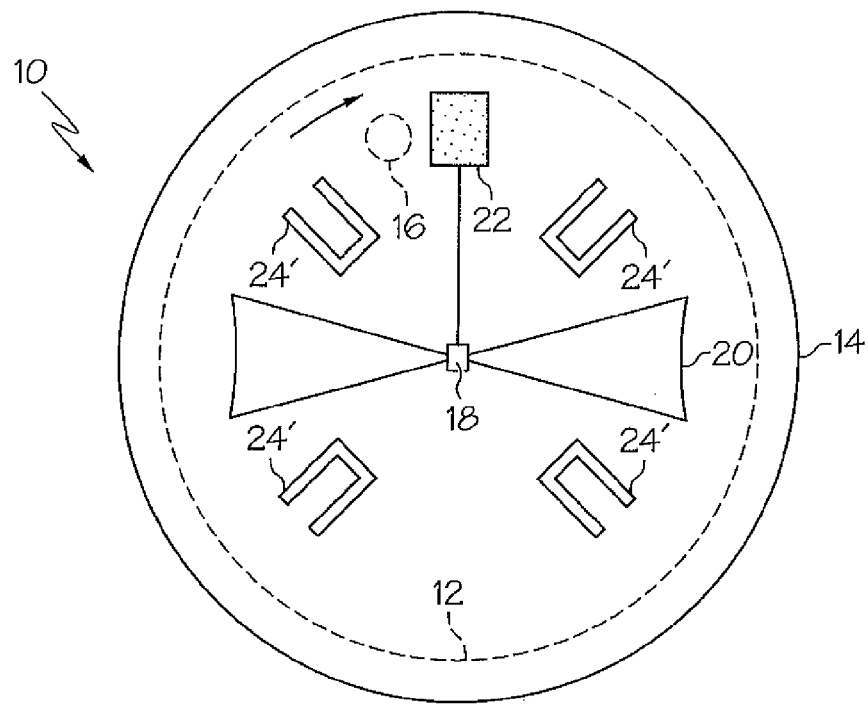
FIG. 3 is a top plan view of an alternative RFID-based sensor featuring selective rotational movement, with the sensor being shown in a closed condition.
Figure 4:
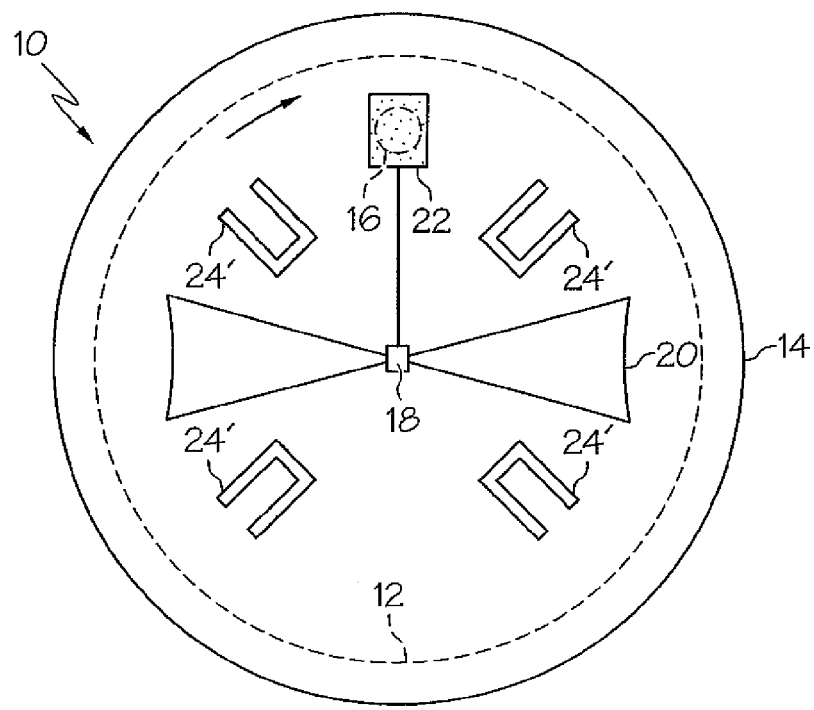
FIG. 4 is a top plan view of the RFID-based sensor of FIG. 3 in an open condition.

In other embodiments, the signal received by the drive element comes from a source which is external to the sensor rather than coming from the chip. For example, FIGS. 3 and 4 illustrate a sensor 26 which is structurally similar to the sensor 10 of FIGS. 1 and 2, except that the one or more drive elements 24' are not electrically connected to the chip 18. Other than this difference, the sensor 26 of FIGS. 3 and 4 is structurally and functionally similar to the sensor 10 of FIGS. 1 and 2. The signal received by the drive element 24' of FIGS. 3 and 4 may be generated by any of a number of different types of external sources. For example, in one embodiment, the drive element 24' receives a signal from an external acoustic source.

Figure 5:
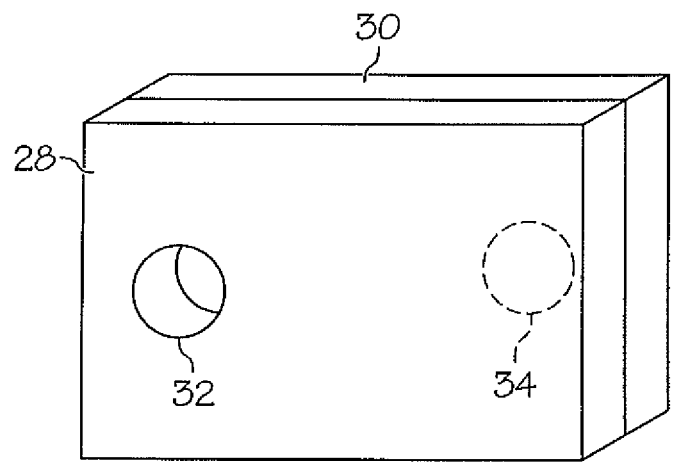
FIG. 5 is a schematic view of an RFID-based sensor featuring selective non-rotational movement, with the sensor being shown in a closed condition.
Figure 6:
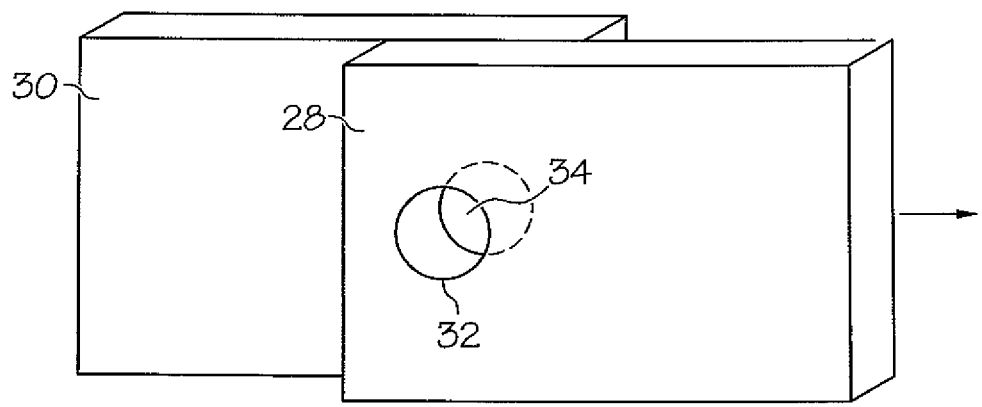
FIG. 6 is a schematic view of the RFID-based sensor of FIG. 5 in an open condition.

The embodiments of FIGS. 1-4 illustrate drive elements which are associated with the layers of a sensor in such a way that the stress manifests itself in the form of a mechanical vibration which causes rotational movement of the two layers with respect to each other. In alternative embodiments, the layers (or portions thereof) of a sensor may move non-rotationally with respect to each other. For example, FIGS. 5 and 6 schematically illustrate a first member 28 and a second member 30 of a sensor, with the two being non-rotationally movable between a closed condition (FIG. 5) and an open condition (FIG. 6). The exact nature of the first and second members 28 and 30 may vary, depending on the nature of the sensor and the use for which it is contemplated. In one embodiment, the first member 28 represents an upper layer and the second member 30 represents a lower layer (similar to that of the sensors 10 and 26 of FIGS. 1-4), while element 32 of the first member 28 represents an aperture and element 34 of the second member 30 represents a sensing material.

In the closed condition of FIG. 5, the aperture 32 of the first member 28 is substantially misaligned with sensing material 34 of the second member 30. When the drive element of the sensor is suitably triggered (e.g., by either receiving a signal, removing a signal, or changing a signal), it causes the first and/or second members 28 and 30 to non-rotationally shift a defined distance to place the aperture 32 in substantial alignment with the sensing material 34 (FIG. 6). So aligning the aperture 32 and the sensing material 34 places the sensing material 34 in fluid communication with the outside environment (via the aperture 32) and allows for analysis thereof.

Figure 7:
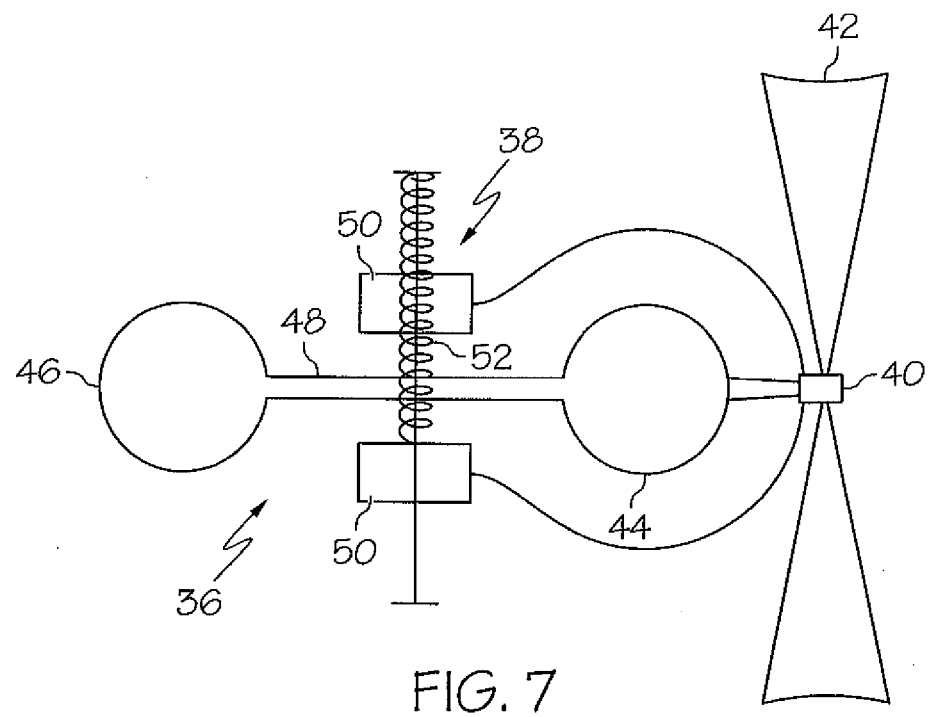
FIG. 7 is a schematic view of an alternative RFID-based sensor featuring selective non-rotational movement, with the sensor being shown in a closed condition.
Figure 8:
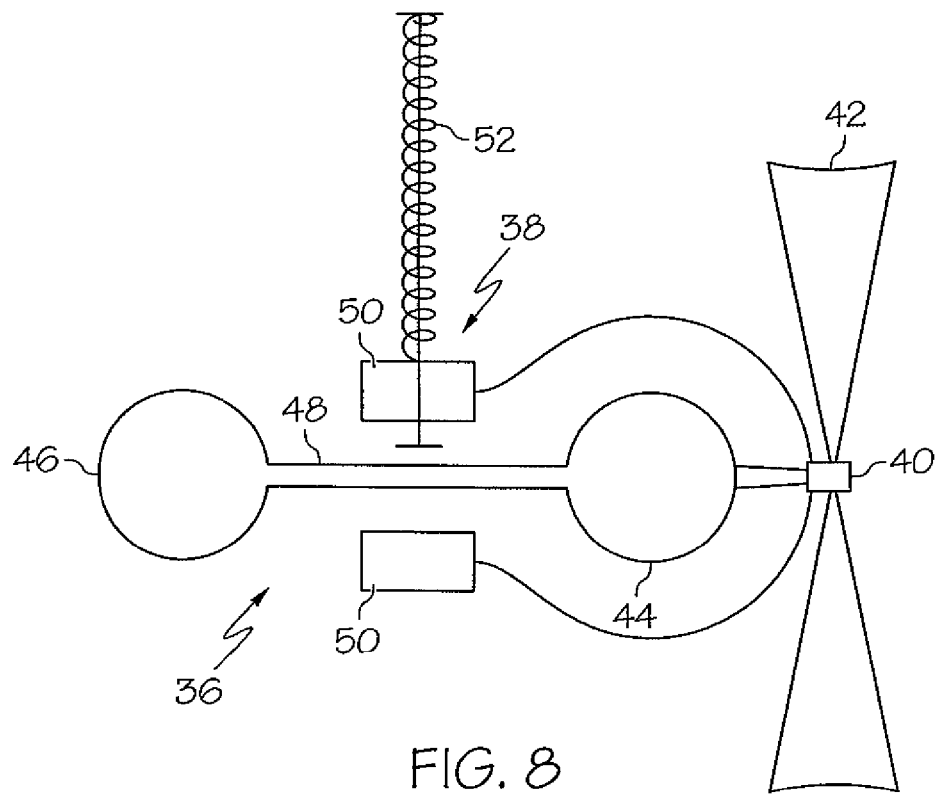
FIG. 8 is a schematic view of the RFID-based sensor of FIG. 7 in an open condition.

In an alternative embodiment, the first and second members 28 and 30 of FIGS. 5 and 6 represent components of a gate valve which is part of a layer or cover overlaying a sensing material of a sensor. In such an embodiment, the element 32 of the first member 28 represents a first aperture and the element 34 of the second member 30 represents a flow path or second aperture leading to the sensing material. In the closed condition of FIG. 5, the aperture 32 of the first member 28 is substantially misaligned with aperture 34 of the second member 30, preventing fluid communication between the outside environment (adjacent to the first member 28) and a sensing material (adjacent to the second member 30). When the drive element of the sensor is suitably triggered (e.g., by either receiving a signal, removing a signal, or changing a signal), it causes the first and/or second members 28 and 30 to non-rotationally shift a defined distance to place the apertures 32 and 34 and in substantial alignment (FIG. 6). So aligning the apertures 32 and 34 places the underlying sensing material in fluid communication with the outside environment and allows for analysis thereof. FIGS. 7 and 8 show an example of a sensor 36 with a gate valve 38 according to this embodiment.

In the embodiment of FIGS. 7 and 8, the sensor 36 includes an RFID chip 40, an antenna 42, and a sensing material 44 in accordance with the foregoing description. An aperture 46 and channel or flow path 48 place the sensing material 44 in fluid communication with the outside environment. The sensor 36 further includes a gate valve 38 which comprises one or more drive elements 50 and a gate member 52 extending across the flow path 48 when the sensor 36 is in a closed condition (FIG. 7). In the illustrated embodiment, the drive elements 50 are electrically connected to the chip 40, but they may be disconnected therefrom in accordance with the foregoing discussion of the sensor 26 of FIGS. 3 and 4.

When the drive elements 50 of the sensor 36 are suitably triggered (e.g., by either receiving a signal, removing a signal, or changing a signal), they cause the gate member 52 to move to a configuration which allows fluid flow through the flow path 48 (FIG. 8), thereby allowing the sensing material 44 to analyze the outside environment. Depending on the nature of the gate member 52, its movement to open the flow path 48 may vary. For example, in one embodiment (shown in FIGS. 7 and 8) the gate member 52 moves non-rotationally to at least partially vacate the flow path 48, thereby allowing fluid flow therethrough. In another embodiment, the gate member 52 comprises a pivotal member (e.g., a butterfly valve) which is rotatable from a closed condition which blocks the flow path 48 to an open condition which at least partially opens the flow path 48. Other types of gate members and opening movements also may be employed without departing from the scope of the present disclosure.

Figure 9:
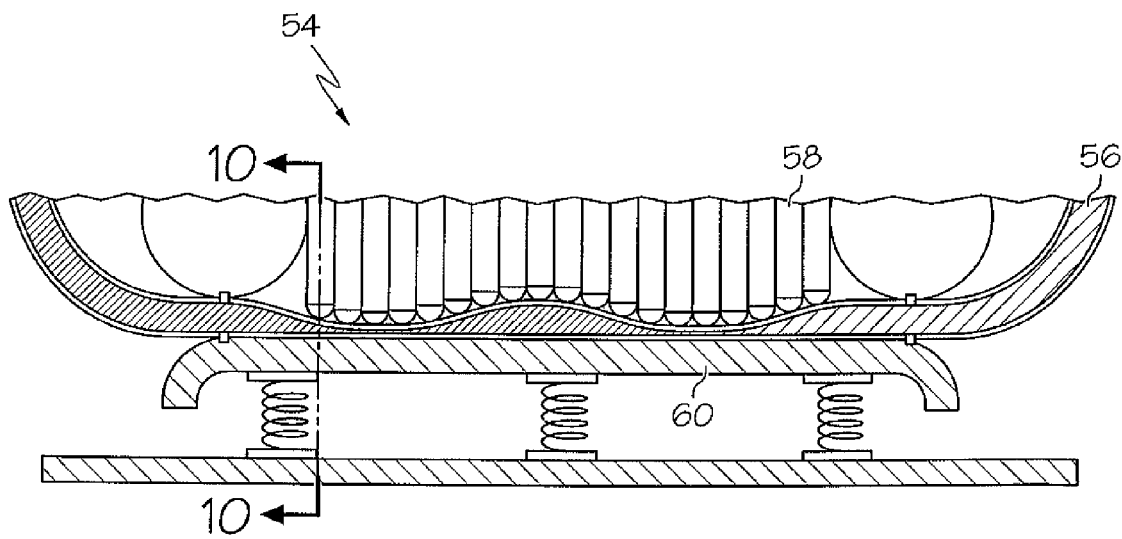
FIG. 9 is a schematic view of another alternative RFID-based sensor featuring selective non-rotational movement.
Figure 10:
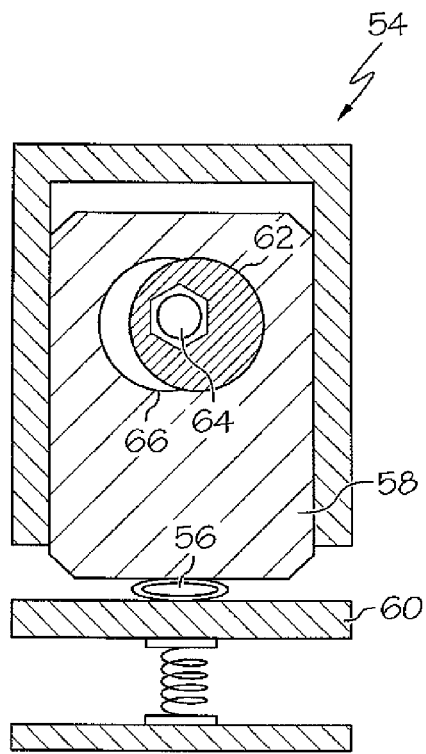
FIG. 10 is a cross-sectional view of the sensor of FIG. 9, taken through the line 10-10 of FIG. 9.

FIGS. 9 and 10 illustrate a gate member 54 provided as a peristaltic-type pump. In the embodiment of FIGS. 9 and 10, the flow path 56 is provided as a flexible channel or tube which extends between a region in the vicinity of the outside environment and a region in the vicinity of a sensing material. The flow path 56 is positioned between a plurality of plates 58 and a backing member 60. The plates 58 are associated with one or more drive elements which, when properly triggered by an input signal, move each plate 58 in a reciprocating manner to move the plates 58 into and out of occlusive contact with the flow path 56. When a plate 58 is in occlusive contact with the flow path 56, it flattens the flow path 56 against the backing member 60 to substantially prevent fluid flow therethrough. When a plate 58 is out of occlusive contact with the flow path 56, the flow path 56 is at least partially un-flattened, allowing fluid flow therethrough.

FIG. 10 shows an exemplary mechanism by which the plates 58 may be moved into and out of occlusive contact with the flow path 56. In the illustrated embodiment, each plate 58 is provided with a cam member 62 which rotates about an off-center pivot 64 in an opening 66 of the plate 58 to move the plate 58 toward and away from the flow path 56. The cam member 62 is rotated by a drive element according to the foregoing description of a drive element which functions to induce rotational movement within a sensor. Other means for inducing reciprocating motion in the plates 58 also may be employed without departing from the scope of the present disclosure.

As shown in FIG. 9, the plates 58 are not all in the same position at the same time, but are instead actuated in a "wave" pattern to move fluid in the flow path 56 from one side of the gate member 54 to the other. In particular, the motion of each plate 58 is slightly delayed with respect to the same motion of the plate 58 upstream of it (i.e., closer to the outside environment). In other words, a plate 58 will be driven into and out of occlusive contact with the flow path 56, while the adjacent downstream plate 58 is driven through substantially the same motion pattern, but slightly delayed in comparison to the upstream plate (i.e., at one point in time the upstream plate 58 is in occlusive contact with the flow path 56 while the downstream plate 58 is partially flattening the flow path 56 and then at the next point in time the upstream plate 58 is moving out of occlusive contact with the flow path 56 while the downstream plate 58 has moved into occlusive contact with the flow path 56). Such a "wave" pattern of the plates 58 causes fluid to flow through the flow path 56 toward the sensing material, similar to the way that a peristaltic pump would.

While FIGS. 9 and 10 are illustrated with a plurality of plates 58 which combine to move fluid through a flow path 56, it is possible for the same function to be achieved by other means, such as a single piece of material with a flexural wave induced therein by action of a drive element.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. An RFID-based sensor, comprising:
   an RFID chip;
   an antenna electrically connected to the RFID chip;
   a sensing material electrically connected to the antenna;
   a first layer with the sensing material associated with the first layer;
   a second layer;
   a drive element, wherein the drive element is configured to move at least a portion of the first and/or second layers with respect to each other upon receiving a signal; and
   the second layer includes at least one aperture, and the at least a portion of the first and/or second layers is movable between a closed condition in which the aperture is substantially misaligned with the sensing material to prevent fluid communication between the sensing material and the outside environment and an open condition in which the aperture is substantially aligned with the sensing material to allow fluid communication between the sensing material and the outside environment.

2. The sensor of claim 1, wherein the drive element is configured to place said at least a portion of the first and/or second layers in the closed condition when not receiving a signal and to place said at least a portion of the first and/or second layers in the open condition when receiving a signal.

3. The sensor of claim 1, wherein the drive element is configured to rotate said at least a portion of the first and/or second layers with respect to each other upon receipt of a signal by the drive element.

4. The sensor of claim 1, wherein the drive element is electrically connected to the RFID chip and configured to receive a signal from the RFID chip.

5. The sensor of claim 1, wherein the drive element is not electrically connected to the RFID chip and is configured to receive a signal from an external source.

6. The sensor of claim 1, wherein the RFID chip, the antenna, the sensing material, and the drive element are associated with the same layer.

7. The sensor of claim 1, wherein the drive element is configured to non-rotationally move said at least a portion of the first and/or second layers with respect to each other upon receipt of a signal by the drive element.

* * * * *